(12) United States Patent
Alexander

(10) Patent No.: US 7,230,696 B2
(45) Date of Patent: Jun. 12, 2007

(54) CALIBRATION OF INSTRUMENTS FOR MEASURING THE PERMEABILITY OF A MATERIAL

(75) Inventor: Bogdan N. Alexander, Richmond, VA (US)

(73) Assignee: Philip Morris USA Inc., Richmond, VA (US)

(*) Notice: Subject to any disclaimer, the term of this patent is extended or adjusted under 35 U.S.C. 154(b) by 346 days.

(21) Appl. No.: 10/854,438

(22) Filed: May 26, 2004

(65) Prior Publication Data
US 2005/0195391 A1 Sep. 8, 2005

Related U.S. Application Data

(60) Provisional application No. 60/551,454, filed on Mar. 8, 2004.

(51) Int. Cl.
*G01J 1/10* (2006.01)

(52) U.S. Cl. ............................. 356/243.1; 356/238.1; 356/238.2

(58) Field of Classification Search .. 356/243.1–243.8, 356/432–444, 238.1–238.2; 250/252.1; 131/281, 905
See application file for complete search history.

(56) References Cited

U.S. PATENT DOCUMENTS

| | | | |
|---|---|---|---|
| 2,528,158 A | 10/1950 | Menke | |
| 2,916,179 A * | 12/1959 | Monroe | .................... 220/560.1 |
| 3,669,543 A * | 6/1972 | Vaccaro | ........................ 356/42 |
| 4,025,752 A | 5/1977 | Whitman, III | |
| 4,218,606 A | 8/1980 | Whitman, III | |
| 4,219,727 A | 8/1980 | Bolt | |
| 4,224,497 A | 9/1980 | Duley et al. | |
| 4,224,498 A | 9/1980 | Grollimund et al. | |
| 4,246,775 A | 1/1981 | Stultz | |
| 4,247,754 A | 1/1981 | Baier | |
| 4,265,254 A * | 5/1981 | Koch et al. | .................. 131/281 |
| 4,281,670 A | 8/1981 | Heitmann et al. | |
| 4,297,559 A | 10/1981 | Whitman, III | |
| 4,383,435 A | 5/1983 | Hinzmann | |
| 4,390,032 A | 6/1983 | Labbe et al. | |
| 4,410,785 A | 10/1983 | Lilly, Jr. et al. | |
| 4,439,663 A | 3/1984 | Lilly, Jr. et al. | |
| 4,537,206 A | 8/1985 | Lorenzen et al. | |
| 4,569,359 A | 2/1986 | Nowers et al. | |
| 4,916,272 A | 4/1990 | Okumoto et al. | |
| 5,092,350 A | 3/1992 | Arthur et al. | |

(Continued)

FOREIGN PATENT DOCUMENTS

GB 1 588 980 5/1981

(Continued)

*Primary Examiner*—Layla Lauchman
*Assistant Examiner*—Tri Ton
(74) *Attorney, Agent, or Firm*—Connolly Bove Lodge & Hutz LLP

(57) ABSTRACT

A system that calibrates instruments for measuring the light or air permeability of a material, and includes a calibration target which can be used for calibration of either light-based or air-based instruments. The calibration target simulates the material whose permeability is being measured, and includes a plate having multiple, angled or parallel rows of perforations provided therethrough. The permeability measuring instrument measures the permeability of the calibration target, and compares the measured permeability with a predetermined permeability of the calibration target and calibrates the permeability measuring instrument based upon the comparison.

24 Claims, 2 Drawing Sheets

U.S. PATENT DOCUMENTS

| | | |
|---|---|---|
| 5,341,824 A | 8/1994 | Fletcher et al. |
| 5,367,144 A | 11/1994 | Matsumura et al. |
| 5,404,889 A | 4/1995 | Belvederi et al. |
| 5,455,119 A * | 10/1995 | Taylor et al. ............... 428/632 |
| 5,754,294 A * | 5/1998 | Jones et al. ................. 356/503 |
| 6,025,572 A | 2/2000 | Imai et al. |
| 6,049,057 A | 4/2000 | Imai et al. |

FOREIGN PATENT DOCUMENTS

GB    1 604 467    12/1981

* cited by examiner

CALIBRATION OF INSTRUMENTS FOR MEASURING THE PERMEABILITY OF A MATERIAL

CLAIM FOR PRIORITY

The present application claims priority of U.S. Provisional Patent Application Ser. No. 60/551,454, filed Mar. 8, 2004, the disclosure of which being incorporated by reference herein in its entirety.

BACKGROUND OF THE INVENTION

A. Field of the Invention

The present invention relates generally to instruments for measuring the permeability of a material, and, more particularly to calibration of instruments for measuring the permeability of a material.

B. Description of the Related Art

Many products or materials are provided with holes or perforations. Such products and materials require their permeability to be measured. Examples of such products and materials needing permeability measurements include: wallpaper; filters used for air, chemicals, etc.; materials affording the appropriate degree of liquid (ink, varnish, sizing) absorption in printing; porous bags and materials used in food packaging and agricultural fumigation; insulating materials; paper; textiles; etc.

One particular material provided with such holes or perforations are the wrappers of filter cigarettes or similar rod-shaped tobacco products. The perforations allow cool atmospheric air to enter the column of tobacco smoke. Such wrappers are called tipping paper. Running webs of tipping paper making up rod-shaped tobacco products may be perforated mechanically, electrically, or optically. For example, British Patent No. 1,588,980 discloses a perforating unit that employs a set of needles or analogous mechanical perforating tools that puncture selected portions of the running web. U.S. Pat. No. 2,528,158 and British Patent No. 1,604,467 disclose electro-perforating tools that employ heat-generating electrodes that combust selected portions of the running web. An optical perforating tool, as disclosed in U.S. Pat. No. 4,265,254, uses coherent radiation from a laser to make perforations of a desired size and with a high degree of reproducibility.

Conventional filter-tipped tobacco products are perforated in the region of their filter plugs to insure that atmospheric air can enter the column of tobacco smoke irrespective of the length of combusted portion of the tobacco-containing section of the product. It is desirable to regulate the permeability of wrappers of all articles of a given tobacco product in such a way that the permeability is consistent or deviates only negligibly from a predetermined value.

Conventionally, closed-loop monitoring systems regulate and control the permeability of rod-shaped tobacco products. Such monitoring systems typically include a sensor(s) or measuring instrument(s) whose feedback is used to adjust the perforating unit if the permeability of the perforated web deviates from an optimum value, as described in U.S. Pat. No. 4,246,775. As set forth in U.S. Pat. No. 4,537,206, two types of sensors are generally used with such monitoring systems to measure permeability: (1) air permeability measuring sensors, and (2) light permeability measuring sensors.

Both air and light permeability measuring instruments need to be periodically calibrated. In general, such instruments are calibrated with certified standards. Conventional air permeability measuring instruments may be statically calibrated using certified standards made of a variety of materials. Calibration of a light permeability measuring instrument must be done dynamically and must use special standards. Current light permeability measuring instruments are calibrated online using a slow-moving perforated tipping paper provided between a light source and a light sensor. This method is inaccurate due to the inherent variability introduced by the tipping paper perforation and due to the residual light penetrating the paper through the non-perforated area. Unfortunately, no calibration standards exist which may be used to calibrate both air and light permeability measuring instruments.

Thus, there is a need in the art to provide a calibration standard that overcomes the problems of the related art and may be used with both air permeability measuring instruments and light permeability measuring instruments.

SUMMARY OF THE INVENTION

The present invention solves the problems of the related art by providing calibration standards, apparatuses, and methods for instruments that measure the permeability of a material.

In accordance with the purpose of the invention, as embodied and broadly described herein, the invention is broadly drawn to a system for calibrating permeability measuring instruments that measure the permeability of a material having perforations or holes. The system includes a calibration target that simulates the material. The system may also include a device to move the calibration target when the system is used to calibrate light permeability measuring instruments. The calibration target may be made of a plate having multiple perforations provided therethrough. The permeability measuring instrument (to be calibrated) measures the permeability of the calibration target, and a comparison is made between the measured and predetermined permeabilities of the calibration target. The permeability measuring instrument is then calibrated based upon the comparison.

Further in accordance with the purpose of the invention, as embodied and broadly described herein, the invention is broadly drawn to a calibration target for calibrating an instrument that measures the permeability of a material having perforations. The calibration target consists of a plate having multiple perforations provided therethrough, wherein the calibration target simulates the perforated material. The calibration target of the present invention can be used to calibrate both air and light permeability measuring instruments. Since the system and calibration target of the present invention may be used to calibrate a light permeability measuring instrument, the calibration target is preferably made from a material that is opaque to light. The calibration target also preferably includes two gaskets. The plate of the calibration target will then be provided between the two gaskets, and the two gaskets will have multiple corresponding windows provided therein for exposing the multiple perforations provided in the plate.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. It is to be understood that both the foregoing general description and the following detailed description are exemplary and explanatory only and are not restrictive of the invention, as claimed.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF EMBODIMENTS OF THE INVENTION

The following detailed description of the invention refers to the accompanying drawings. The same reference numbers in different drawings identify the same or similar elements. Also, the following detailed description does not limit the invention. Instead, the scope of the invention is defined by the appended claims and equivalents thereof.

Figure 1:
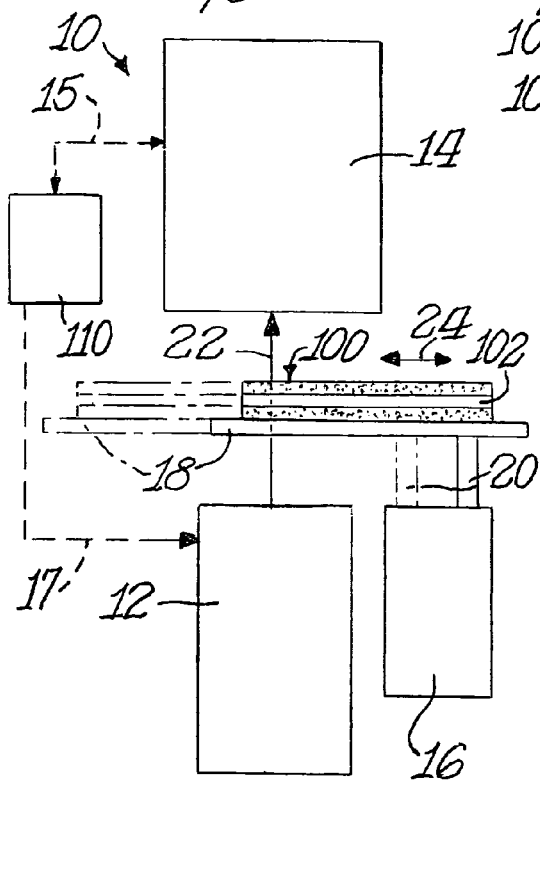
FIG. 1 is a schematic elevational view showing a system for calibrating light permeability measuring instruments in accordance with an embodiment of the present invention.

A system for calibrating an instrument for measuring the light permeability of a material in accordance with an embodiment of the present invention is shown generally as reference numeral 10 in FIG. 1. As used herein, the term "material" includes, but is not limited to, products or materials with holes or perforations that require their permeability to be measured. Examples of such products and materials needing permeability measurements include: wallpaper; filters used for air, chemicals, etc.; materials affording the appropriate degree of liquid (ink, varnish, sizing) absorption in printing; porous bags and materials used in food packaging and agricultural fumigation; insulating materials; paper; textiles; wrappers of filter cigarettes or similar rod-shaped tobacco products; etc.

System 10 includes light-based permeability measuring instruments, such as, for example, a light or laser source 12 and an optical sensor 14, a translation device 16 attached in between laser source 12 and optical sensor 14, an oscillating frame 18 driven by translation device 16 with a mechanism 20 (e.g., a rack-and-pinion driven by a motor turning clockwise and then anti clockwise, moving oscillating frame 18), and a calibration target 100 attached to the oscillating frame 18. Calibration target 100 consists of a plate 102 sandwiched between a pair of gaskets 104. Oscillating frame 18 oscillates calibration target 100 back and forth, via mechanism 20, as shown in phantom lines in FIG. 1.

Laser source 12 and optical sensor 14 may comprise any conventional light source and optical sensor used to measure permeability, such as, for example, the laser source and optical detector arrangement disclosed in U.S. Pat. No. 4,537,206. More specifically, the present invention may be used with the light permeability measuring system disclosed in co-pending U.S. patent application Ser. No. 10/854,338, filed concurrently herewith) assigned to the assignee of the present invention, Philip Morris USA, Inc. Laser source 12 and optical sensor 14 are components of the light permeability measuring instrument to be calibrated.

Oscillating frame 18 may move calibration target 100 back and forth (as shown by arrow 24) a number of times in between a light beam 22. Light beam 22 may be a very thin line of light, e.g., ten millimeters (mm) long and 0.1 mm thick, provided by laser source 12 and received by optical sensor 14. Preferably, oscillating frame 18 moves calibration target 100 back and forth across light beam 22 a predetermined number of times and at a predetermined velocity. For example, oscillating frame 18 may move calibration target 100 across light beam 22 ten times, then the system calculates an average of the ten readings.

For calibration of air-based instruments, laser source 12 and optical sensor 14 are replaced by a conventional pneumatic sensor and pressure detector arrangement, such as, for example, the pneumatic sensor and pressure detector arrangement disclosed in U.S. Pat. No. 4,246,775. More specifically, calibration target 100 of the present invention can be used with air permeability measuring instruments such as the Models A15, A16, and A17 Air Permeability Testers available from Borgwaldt Technik GmbH of Germany, the Paper Permeability Meter (PPM 100 and others) available from Filtrona International, Ltd., etc.

Since Borgwaldt Models A15 and A16 use internal calibration standards, it is inconvenient to calibrate multiple instruments with the same calibration target. However, calibration target 100 of the present invention may be certified by an accredited laboratory by measuring its permeability to air on a certified instrument, and then be used as a certified calibration target 100. With adequate software modifications to the Borgwaldt Models A15, A16, and A17, calibration target 100 of the present invention may be used to quickly and accurately calibrate Models A15, A16, and A17, without taking off the Models' covers. Similarly, calibration target 100 could be used as a certified standard for calibrating light permeability measuring instruments.

In contrast to air permeability measuring instruments (e.g., the Borgwaldt Models A15, A16, and A17 Air Permeability Testers, the Filtrona Paper Permeability Meter (PPM 100), etc.) which work offline, light permeability measuring instruments work online, measuring the permeability of the material to light. Thus, air permeability measuring instruments may be calibrated statically, which eliminates the need for the translation device 16, oscillating frame 18, and mechanism 20 shown in FIG. 1. In contrast, light permeability measuring instruments are calibrated dynamically, with calibration target 100 being moved by oscillating frame 18.

Figure 3:
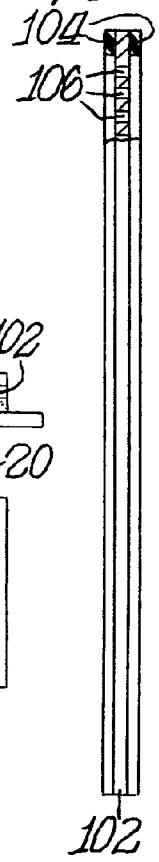
FIG. 3 is a side elevational view of the calibration target shown in FIG. 2, partially broken away.
Figure 2:
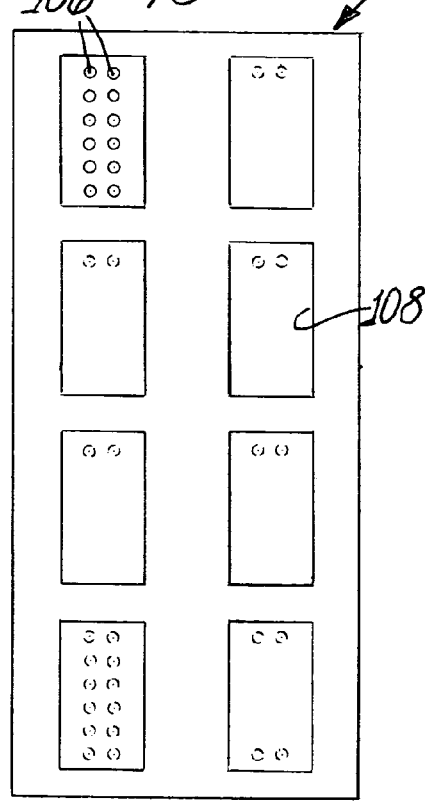
FIG. 2 is a top plan view showing a calibration target used in the system of FIG. 1, the system of FIG. 1 can use the entire calibration target with eight windows or just one single window resulting from cutting the target into eight equal parts, each containing one single window.

As best shown in FIGS. 2 and 3, calibration target 100 is made from a plate 102 having multiple perforations 106 provided therein, and being sandwiched between two gaskets 104 having multiple windows 108 provided therein for exposing portions of plate 102 and perforations 106. Each window 108 provided in one gasket 104 has a corresponding window 108 provided in the other gasket 108, wherein the corresponding windows 108 align with each other. Calibration target 100 simulates a perforated material, which allows an accurate and repeatable measurement on the same or different permeability measurement instruments, comparison of measurements made on different instruments, and comparison between air-based and light-based measuring instruments.

The plate 102 may be made of a material that is substantially opaque to light so that light only penetrates through perforations 106 the same way air does. Given an algorithm to describe the equivalence between air and light permeability, calibration target 100 may be used to calibrate light permeability measuring systems. Plate 102 may be made from a variety of materials, but preferably is made from a material that is stable with environmental changes—a material that has a small thermal dilation coefficient and is substantially insensitive to moisture (e.g., relative humidity)—and may be used a large number of times without degradation or changes in the material characteristics. Thus, plate 102 may be made from metallic materials like stainless steel, aluminum, etc. Preferably, plate 102 is made from a special alloy having the properties described above. For example, a nickel-cobalt combination, made by electrically forming a layer of cobalt on a nickel base, may be used for the material making up plate 102. Such a nickel-cobalt alloy is available from the Metrigraphics division of Dynamics Research Corporation of Andover, Mass.

Plate 102 may also have a variety of geometries and is not limited to the geometry shown in FIGS. 2 and 3. For example, the geometry of plate 102 may depend upon the instrument it is calibrating, and thus, have an application-specific geometry.

The algorithm used with the present invention will be tailored to the specific configuration of the sensor being calibrated. Thus, if the sensor configuration changes, then the algorithm will change as well. For example, a calibration equation which defines the correlation between light permeability and air permeability may be created by measuring two different, previously certified targets with an air-flow measuring instrument and a light measuring instrument. These measurements provide first and second air permeabilities $AP_1$ and $AP_2$ which correlate with first and second light permeabilities $LP_1$ and $LP_2$. These values enable the calibration parameters of the calibration equation to be calculated, namely the slope $C_{slope}$ and the intercept $C_{int}$ of the equation. The calibration equation will thus be $AP=C_{slope} \times LP+C_{int}$, where:

$$C_{slope} = \frac{AP_2 - AP_1}{LP_2 - LP_1}, \text{ and } C_{int} = \frac{LP_2 \times AP_1 - LP_1 \times AP_2}{LP_2 - LP_1}.$$

The calibration equation defines the correlation between light permeability and air permeability, which can be considered linear for a limited range of permeability values. Once the slope $C_{slope}$ and intercept $C_{int}$ are calculated, the light permeability (LP) of a material may be measured, and based upon the calibration equation the equivalent air permeability (AP) of the material may be calculated.

Gaskets 104 may also be made from a variety of materials, but preferably are made from a material that ensures excellent air sealing during calibration of air permeability measuring instruments, and substantially eliminates the possibility of air leakage. Gaskets 104, therefore, may be made from rubber materials (natural or synthetic), elastomeric materials, etc.

Although FIG. 2 shows eight windows 108, calibration target 100 may have any number of windows 108 depending upon the application of calibration target 100, such as, for example, the type of material being measured. Likewise, although FIG. 2 shows six perforation holes per row, with two rows of perforations for each window 108, calibration target 100 may have any number of perforation rows depending upon the application of calibration target 100, such as, for example, the type of material being measured. For example, each window 108 may have one, two, four, six, or eight perforation rows to simulate tipping paper with one, two, four, six, or eight perforation rows. Varying the number of perforations 106 enables calibration target 100 to be built with a wide range of air permeability.

Figure 4:
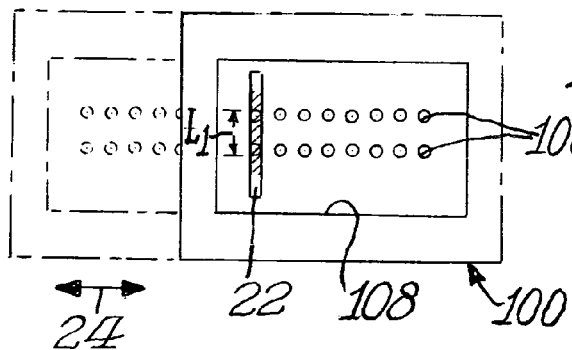
FIG. 4 is a top plan view of the calibration target shown in FIGS. 2 and 3 in a starting position with a light beam and in an extended position shown in outline.

FIG. 4 shows a top plan view of one window 108 of calibration target 100 shown in FIGS. 2 and 3 in a starting position, with a light beam 22, and in an extended position shown in outline. The window 108 shown in FIG. 4 includes perforation rows, with eight perforations 106 per row. The perforations 106 are spaced a distance $L_1$ (either center-to-center or outside-to-outside) corresponding to the distance separating the perforations rows of conventional tipping paper. As further shown in FIG. 4, light beam 22 scans both rows at the same time, as calibration target 100 moves in the side-to-side direction, as shown by arrow 24.

Multiple rows (e.g., four, six, eight, etc.) of perforations 106 can generate light information accurately enough for the purpose of calibrating laser source 12 and optical detector 14. However, two parallel rows and particularly one row of perforations on calibration target 100 may generate an error equal to the inherent differential non-linearity of the cross-profile intensity of laser source 12. The light intensity across the ten millimeter (mm)-long line of laser source 12 (scanning the perforations) usually has variations. Such variations are called "integral non-linearity" for the entire ten mm length of the light line, and they can reach up to 10% of the nominal intensity. Whereas variations are called "differential non-linearity" for contiguous small segments of the ten mm length, which can reach up to 3-4% of the nominal intensity. This is explained in more details in U.S. patent application Ser. No. 10/854,338, Invention Disclosure No. D1615.

Figure 5:
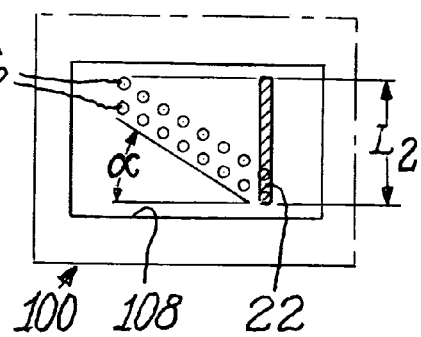
FIG. 5 is a top plan view showing another calibration target used in the system of FIG. 1.

Accordingly, in order to reduce the error, as shown in FIG. 5, one or more windows 108 of calibration target 100 may include up to eight angled perforation rows. When calibrating the light permeability measuring instruments, only one window of the eight existing windows on calibration target 100 is used. This is accomplished by simply cutting calibration target 100 into eight pieces. However, an entire target 100 containing eight windows is preferably used for air permeability instruments, as it can include eight different values for calibration. Instruments like the Borgwaldt Models A15, A16, and A17 have two measuring channels that can both be calibrated in one step using two adjacent windows with equal, known permeability. By using eight windows, four different calibration values, covering a large range of permeability, may be provided on a single plate. The perforation rows are angled at an angle $\alpha$ and designed to fit within the length $L_2$ (from the topmost perforation 106 to the bottommost perforation 106), where length $L_2$ is equal to or smaller than the length of light beam 22. Angle $\alpha$ may have various sizes, but is sized to ensure that, in connection with length $L_2$, during the scanning process the entire length of light beam 22 (ten mm) will participate in the measurement, and not only a small portion equal to $L_1$. As further shown in FIG. 5, light beam 22 scans perforations 106 as calibration target 100 moves in the side-to-side direction. This way, angled perforations 106 are scanned with a larger area of light beam 22 (that is, $L_2 > L_1$), producing a substantially more accurate result by averaging the inherent variable intensity of the light beam 22.

As discussed above, the system of present invention needs the translation device 16, oscillating frame 18, and mechanism 20 only when calibrating light permeability measuring instruments. However, the calibration target 100 of the present invention can be used in most common air permeability measuring instruments, like the Borgwaldt Models A15, A16, and A17, either in an eight window format or using any of the ⅛ sections. The calibration procedure is well known for the air-based systems: a measuring head blows air through calibration target 100, and the system measures the air flow through a particular size area in a particular duration of time.

The operation of calibration system 10 of the present invention, as applied to light permeability measuring instruments, includes moving calibration target 100 back and forth (as shown by arrow 24), with oscillating frame 18, a number of times in between the light beam 22 generated by laser source 12 and received by optical sensor 14. The oscillation motion of calibration target 100 simulates the movement of the material. Light beam 22 scans perforations 106 provided in calibration target 100, and optical sensor 14 receives the light beams 22 traveling through perforations 106, and generates a signal 15 proportional to the amount of light passed through calibration target 100 during each oscillation. Laser source 12 is controlled by a signal 17 provided by a computing device 110. Motorized translation device 16, via mechanism 20, drives oscillating frame 18 on which calibration target 100 is attached. Signal 15 is also provided to computing device 110. Signal 15 is measured by the instrument to be calibrated (i.e., laser source 12 and optical sensor 14), and computing device 110 averages the values obtained and produces an output that is the light permeability equivalent of the air permeability of calibration target 100. Knowing the air permeability of calibration target 100 (a certified value, which may be obtained as described previously), an equivalency can be derived to calibrate the light permeability measuring instrument, including laser source 12 and optical sensor 14, using an algorithm as discussed above.

Although FIG. 1 shows laser source 12, optical sensor 14, and computing device 110 as separate elements, these three structures may be housed in and make up a single light permeability measuring instrument. Alternately, computing device 110 may be a separate structure and laser source 12 and optical sensor 14 may be housed in and make up a single light permeability measuring instrument.

Computing device 110 represents a combination of hardware and software, and thus may comprise a conventionally programmed computer, a programmed logic controller ("PLC"), a microcontroller embedded with software, or any other intelligent system.

Figure 6:
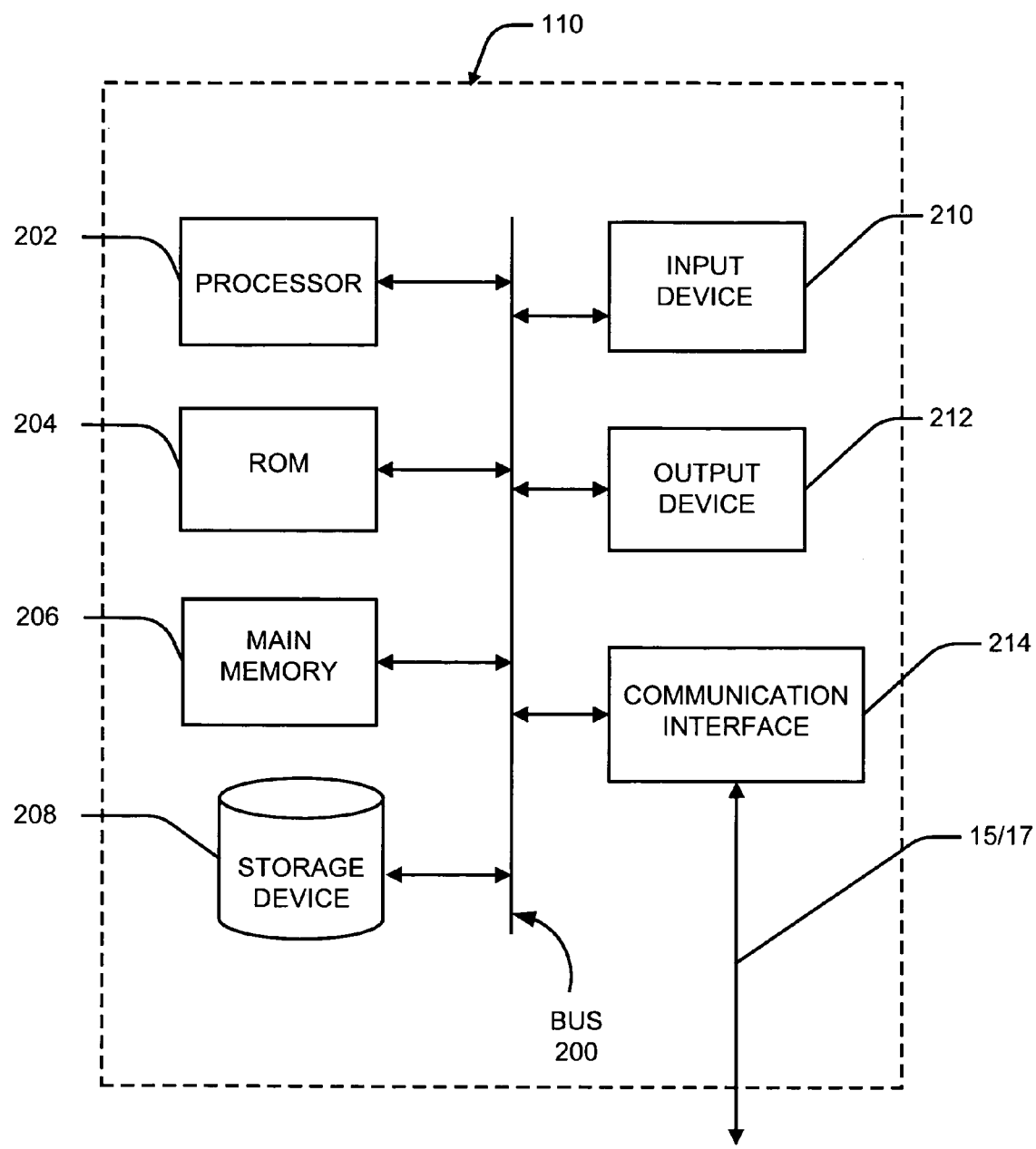
FIG. 6 is a schematic diagram showing a computing device capable of use with the system of FIG. 1.

Referring to FIG. 6, if computing device 110 is a conventionally programmed computer, then such a computer may include a bus 200 interconnecting a processor 202, a read-only memory (ROM) 204, a main memory 206, a storage device 208, an input device 210, an output device 212, and a communication interface 214. Bus 200 is a network topology or circuit arrangement in which all devices are attached to a line directly and all signals pass through each of the devices. Each device has a unique identity and can recognize those signals intended for it. Processor 202 includes the logic circuitry that responds to and processes the basic instructions that the drive computer. ROM 204 includes a static memory that stores instructions and data used by processor 202.

Computer storage is the holding of data in an electromagnetic form for access by a computer processor. Main memory 206, which may be a RAM or another type of dynamic memory, makes up the primary storage of the computer. Secondary storage of the computer may comprise storage device 208, such as hard disks, tapes, diskettes, Zip drives, RAID systems, holographic storage, optical storage, CD-ROMs, magnetic tapes, and other external devices and their corresponding drives. Main memory 206 and/or storage device 208 may store any of the data retrieved from any of the components of the present invention.

Input device 210 may include a keyboard, mouse, pointing device, sound device (e.g. a microphone, etc.), biometric device, or any other device providing input to the computer. Output device 212 may comprise a display, a printer, a sound device (e.g. a speaker, etc.), or other device providing output to the computer. Communication interface 214 may include network connections, modems, or other devices used for communications with other computer systems or devices.

Communication links (receiving signals such as signals 15, 17) may be wired, wireless, optical or a similar connection mechanisms. "Wireless" refers to a communications, monitoring, or control system in which electromagnetic or acoustic waves carry a signal through atmospheric space rather than along a wire. In most wireless systems, radio-frequency (RF) or infrared (IR) waves are used. Some monitoring devices, such as intrusion alarms, employ acoustic waves at frequencies above the range of human hearing.

Computing device 110 consistent with the present invention may perform the tasks of receiving signals 15, 17 and producing an output that is the light permeability equivalent of the air permeability of calibration target 100. Knowing the air permeability of calibration target 100 (a certified value, which may be obtained as described previously), an equivalency can be derived to calibrate the light permeability measuring instrument, including laser source 12 and optical sensor 14, using the algorithm as discussed above. Computing device 110 may perform these tasks in response to a processor executing sequences of instructions contained in a computer-readable medium. A computer-readable medium may include one or more memory devices and/or carrier waves.

Execution of the sequences of instructions contained in a computer-readable medium causes the processor to perform the processes described above. Alternatively, hardwired circuitry may be used in place of or in combination with software instructions to implement processes consistent with the present invention. Thus, the present invention is not limited to any specific combination of hardware circuitry and software.

It will be apparent to those skilled in the art that various modifications and variations can be made in the calibration system and target of the present invention and in construction of the system and target without departing from the scope or spirit of the invention. Examples of such modifications have been previously provided.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A system for calibrating an instrument for measuring the light permeability of a perforated material, the system comprising:

a calibration target simulating the perforated material and including a plate having multiple windows with at least two rows of perforations parallel to one another in each window; and a device for repetitively moving said calibration target in an oscillating manner for scanning by a light source.

2. A system for calibrating an instrument for measuring the light permeability of a perforated material, as recited in claim 1, wherein the light permeability measuring instrument measures the permeability of said calibration target, and the measured permeability is compared with a predetermined air permeability of said calibration target to calibrate the light permeability measuring instrument based upon the predetermined air permeability of the calibration target.

3. A system for calibrating an instrument for measuring the light permeability of a perforated material, as recited in claim 1, wherein said device for moving said calibration target comprises an oscillating frame that moves said calibration target in relation to the light permeability measuring instrument to simulate movement of the material.

4. A system for calibrating an instrument for measuring the light permeability of a perforated material, as recited in claim 1, wherein each window of the calibration target includes perforations in parallel rows, and the number of parallel rows in the windows are different from one another.

5. A system for calibrating an instrument for measuring the light permeability of a perforated material, as recited in claim 1, wherein the perforations comprise one or more angled rows of perforations.

6. A system for calibrating an instrument for measuring the light permeability of a perforated material, as recited in claim 1, wherein said calibration target comprises a substantially opaque material.

7. A system for calibrating an instrument for measuring the light permeability of a perforated material, as recited in claim 1, wherein the material comprises a tipping paper for rod-shaped tobacco products.

8. A system for calibrating an instrument for measuring the light permeability of a material, the system comprising:
   a calibration target simulating the material and including a plate having multiple perforations provided therethrough; and
   a device for moving said calibration target, and
   wherein said calibration target further comprises two gaskets, the plate of said calibration target being provided between the two gaskets, the two gaskets having multiple, corresponding windows provided therein for exposing the multiple perforations provided in the plate.

9. A system for calibrating an instrument for measuring the light permeability of a material, the system comprising:
   a calibration target simulating the material and including a plate having multiple perforations provided therethrough; and
   a device for moving said calibration target, and
   wherein the light permeability measuring instrument measures the permeability of said calibration target, and the measured permeability is compared with a predetermined permeability of said calibration target to calibrate the light permeability measuring instrument based upon the comparison further comprising:
   a computer memory for storing the measured and predetermined permeabilities of said calibration target; and
   a computer processor for processing the measured and predetermined permeabilities stored in the computer memory, wherein the computer processor is electrically coupled to the computer memory and compares the measured and predetermined permeabilities of said calibration target to calibrate the light permeability measuring instrument based upon the comparison.

10. A calibration target for calibrating an instrument that measures the air or light permeability of a perforated material, the calibration target comprising:
   a plate having multiple windows with at least two rows of perforations parallel to one another in each window, wherein the calibration target simulates the perforated material.

11. A calibration target for calibrating an instrument that measures the air or light permeability of a perforated material, as recited in claim 10, wherein each window includes perforations in parallel rows, and the number of parallel rows in the windows are different from one another.

12. A calibration target for calibrating an instrument that measures the air or light permeability of a perforated material, as recited in claim 10, wherein the perforations comprise at least two angled rows of perforations.

13. calibration target for calibrating an instrument that measures the air or light permeability of a perforated material, as recited in claim 10, wherein the calibration target comprises a substantially opaque material.

14. A calibration target for calibrating an instrument that measures the air or light permeability of a material, the calibration target comprising:
   a plate having multiple perforations provided therethrough, wherein the calibration target simulates the material, and further comprising:
   two gaskets, said plate of the calibration target being provided between said two gaskets, said two gaskets having multiple, corresponding windows provided therein for exposing the multiple perforations provided in said plate.

15. A calibration target for calibrating an instrument that measures the air or light permeability of a material, as recited in claim 14, wherein said gaskets sealingly connect with an air permeability measuring instrument.

16. A calibration target for calibrating an instrument that measures the air or light permeability of a material, as recited in claim 14, wherein each of said gaskets comprises a material selected from the group consisting of a natural rubber material, a synthetic rubber material, and an elastomeric material.

17. A calibration target for calibrating an instrument that measures the air or light permeability of a material, the calibration target comprising:
   a plate having multiple perforations provided therethrough, wherein the calibration target simulates the material, and
   wherein said plate comprises a material that has a small thermal dilation coefficient and is substantially insensitive to moisture.

18. A calibration target for calibrating an instrument that measures the air or light permeability of a material, the calibration target comprising:
   a plate having multiple perforations provided therethrough, wherein the calibration target simulates the material, and
   wherein said plate comprises a nickel-cobalt alloy made by electrically forming a layer of cobalt on a nickel base.

19. A method for calibrating an instrument for measuring the air permeability of a perforated material, the method comprising:

moving a calibration target that simulates the material and includes a plate having multiple windows with at least two rows of perforations parallel to one another in each window;

measuring the permeability of the calibration target;

using the measured permeability of the calibration target and a predetermined air permeability of the calibration target for determining a calibration equation for the instrument being calibrated;

storing the calibration equation in a memory of the instrument;

using the calibration equation to produce a real value of the measured air permeability of a perforated material; and displaying the real value of the measured air permeability of the perforated material to a user.

20. A method for calibrating an instrument for measuring the air permeability of a material, as recited in claims 19, further comprising:

storing the measured and predetermined permeabilities of the calibration target; and processing the stored permeabilities to compare the measured and predetermined permeabilities of the calibration target and to calibrate the air permeability measuring instrument based upon the comparison.

21. A method for calibrating an instrument for measuring the air permeability of a perforated material, the method comprising:

measuring the permeability of a calibration target that simulates the material and includes a plate having multiple windows with at least two rows of perforations parallel to one another in each window;

using the measured permeability of the calibration target and a predetermined air permeability of the calibration target for determining a calibration equation for the instrument being calibrated;

storing the calibration equation in a memory of the instrument;

using the calibration equation to produce a real value of the measured air permeability of a perforated material; and displayinq the real value of the measured air permeability of the perforated material to a user.

22. A method for calibrating an instrument for measuring the air permeability of a material, as recited in claim 21, further comprising:

storing the measured and predetermined permeabilities of the calibration target; and processing the stored permeabilities to compare the measured and predetermined permeabilities of the calibration target and to calibrate the air permeability measuring instrument based upon the comparison.

23. A system for calibrating an instrument for measuring the light permeability of a material, the system comprising:

a calibration target simulating the material and including a plate having multiple, parallel or angled rows of perforations provided therethrough, wherein said calibration target comprises a substantially opaque material and has a predetermined permeability, and the light permeability measuring instrument measures the permeability of said calibration target;

an oscillating frame that moves said calibration target in relation to the light permeability measuring instrument to simulate movement of the material;

a computer memory for storing the measured and predetermined permeabilities of said calibration target; and a computer processor for processing the measured and predetermined permeabilities stored in the computer memory, wherein the computer processor is electrically coupled to the computer memory and compares the measured and predetermined permeabilities of said calibration target to calibrate the light permeability measuring instrument based upon the comparison.

24. A system for calibrating an instrument for measuring the air permeability of a material, the system comprising:

a calibration target simulating the material and including a plate having multiple, parallel or angled rows of perforations provided therethrough, wherein said calibration target has a predetermined permeability and comprises two gaskets, the plate of said calibration target being provided between the two gaskets, the two gaskets having multiple, corresponding windows provided therein for exposing the multiple perforations provided in the plate, and wherein the air permeability measuring instrument measures the permeability of said calibration target;

a computer memory for storing the measured and predetermined permeabilities of said calibration target; and a computer processor for processing the measured and predetermined permeabilities stored in the computer memory, wherein the computer processor is electrically coupled to the computer memory and compares the measured and predetermined permeabilities of said calibration target to calibrate the air permeability measuring instrument based upon the comparison.

* * * * *